United States Patent [19]

Fujiyama et al.

[11] 3,956,394

[45] May 11, 1976

[54] PROCESS FOR PURIFYING P-TOLUALDEHYDE

[75] Inventors: Susumu Fujiyama; Minoru Takagawa, both of Niigata, Japan

[73] Assignee: Mitsubishi Gas Chemical Company, Inc., Tokyo, Japan

[22] Filed: Sept. 30, 1974

[21] Appl. No.: 510,610

[30] Foreign Application Priority Data

Oct. 11, 1973    Japan................................ 48-114074

[52] U.S. Cl. ................................................. 260/599
[51] Int. Cl.² ........................................ C07C 45/24
[58] Field of Search ..................................... 260/599

[56] References Cited
UNITED STATES PATENTS

| | | | |
|---|---|---|---|
| 2,462,739 | 2/1949 | Gresham............................ | 260/599 |
| 2,485,237 | 10/1949 | Gresham et al..................... | 260/599 |
| 2,534,017 | 12/1950 | Gresham et al..................... | 260/599 |
| 3,284,508 | 11/1966 | Gray et al............................ | 260/599 |
| 3,369,048 | 2/1968 | Hamilton et al..................... | 260/599 |
| 3,636,157 | 1/1972 | Bozik et al.......................... | 260/599 |

OTHER PUBLICATIONS

Wolf, "Chem. Abstracts", Vol. 71, p. 38588b, (1969).

*Primary Examiner*—Norman Morgenstern
*Attorney, Agent, or Firm*—Armstrong, Nikaido & Wegner

[57] ABSTRACT p-Tolualdehyde is separated with a high purify from a mixture of tolualdehyde isomers having a mole fraction of p-tolualdehyde of at least 0.27, on the basis of total tolualdehyde isomers by cooling the mixture to a crystallization temperature of −6° to −60°C, thereby crystallizing p-tolualdehyde, and separating the resulting p-tolualdehyde crystals from mother liquor. A solvent such as an aliphatic hydrocarbon having 1 to 9 carbon atoms or an alicyclic hydrocarbon having 3 to 9 carbon atoms can be added to the mixture before cooling to improve the crystallization conditions. The resulting crystals can be washed with a washing agent, such as said solvent, to remove the other isomers adhering to the crystals.

18 Claims, 1 Drawing Figure

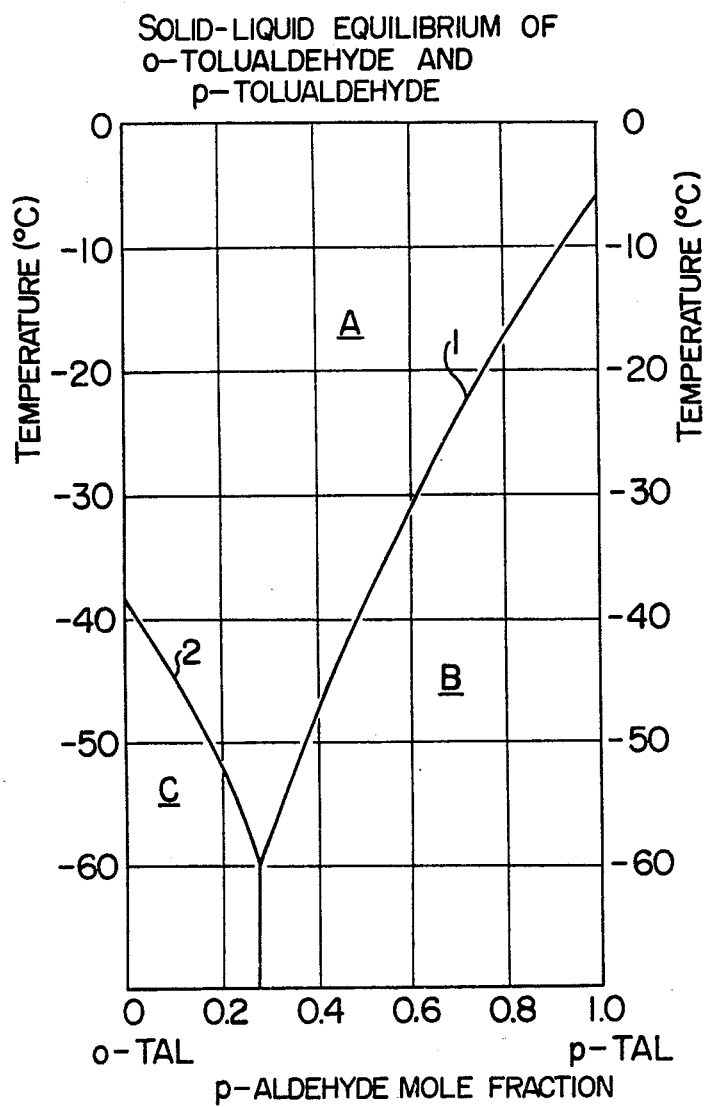

PROCESS FOR PURIFYING P-TOLUALDEHYDE

This invention relates to a process for purifying p-tolualdehyde, and more particularly to a process for purifying p-tolualdehyde, which comprises cooling a mixture of tolualdehyde isomers to a temperature of −6° to −60°C, thereby crystallizing p-tolualdehyde, and separating the resulting p-tolualdehyde crystals from o-tolualdehyde and m-tolualdehyde in mother liquor, thereby obtaining substantially pure p-tolualdehyde.

Generally, p-tolualdehyde is obtained by reaction of toluene with carbon monoxide in the presence of a Friedel-Crafts catalyst such as $HF-BF_3$, $HCl-AlCl_3$, etc. The resulting p-tolualdehyde usually contains a few to ten or more percent of o-tolualdehyde and a small amount of m-tolualdehyde. For example, p-tolualdehyde obtained by means of said $HF—BF_3$ catalyst usually contains 3 to 5% of o-tolualdehyde, and p-tolualdehyde obtained by means of said $HCl-AlCl_3$ catalyst usually contains 10 to 15% of o-tolualdehyde and a very small amount of m-tolualdehyde. Further, p-tolualdehyde can be also obtained by partial oxidation of xylene by means of air, oxygen or other oxidizing agent. p-Tolualdehyde containing o-tolualdehyde and m-tolualdehyde, obtained in these processes, will be hereinafter referred to as crude p-tolualdehyde.

p-Tolualdehyde is used as a raw material for terephthalic acid, or a starting material for polyester fiber raw material through hydroxymethylbenzoic acid, raw material for producing polyparaxylene derivatives, etc., and p-cresol can be derived from p-tolualdehyde by oxidation with a peracid. Thus p-tolualdehyde is useful as a starting material for various uses. When p-tolualdehyde is used in various uses, the crude p-tolualdehyde can be used as such, depending upon the uses, but a higher purity is preferable, if possible. Especially, when p-tolualdehyde is used as a starting material for terephthalic acid as a fiber raw material or polyester fiber raw material, a higher purity is required for p-tolualdehyde.

Heretofore, Japanese Patent No. 449977 discloses the purity of p-tolualdehyde synthesized by carbonylation of toluene in the presence of a $HF—BF_3$ catalyst, but studies or disclosure have not been made yet about purification of crude p-tolualdehyde containing o-tolualdehyde and m-tolualdehyde and production of p-tolualdehyde of higher purity containing no other isomers.

As described above, the crude p-tolualdehyde synthesized by cabonylation of toluene is substantially a mixture of p-tolualdehyde and a few to ten or more percent of o-tolualdehyde containing a very small amount of m-tolualdehyde. Further, the crude p-tolualdehyde obtained by oxidation of xylene is presumed to have a composition of tolualdehyde isomers in various proportion, based on an isomer composition of the raw material xylene. Boiling points of these o-, m-and p-tolualdehydes are 196° to 199°C, 199°C and 204° to 206°C, respectively. Thus, the boiling points of these isomers are so close to one another that it is not always advantageous to obtain pure p-tolualdehyde from a mixture of tolualdehyde isomers by distillation.

As a result of various studies of obtaining p-tolualdehyde of higher purity from the mixture of tolualdehyde isomers, the present inventors have established the present invention. As described above, the boiling points of these three isomers are well known, but freezing points of these three isomers have not been known yet. That is, it has been quite unclear what freezing points they have and in what manner they behave. As a result of measuring the freezing points of these three tolualdehyde isomers, it has been found that o-tolualdehyde has a freezing point of −39.0°C, m-tolualdehyde −42.0°C and p-tolualdehyde −5.6°C. Further, it has been found that there are no substantial differences in mutual solubility between o-tolualdehyde and p-tolualdehyde and that between m-tolualdehyde and p-tolualdehyde, and further that a solid-liquid equilibrium relation between o-tolualdehyde and p-tolualdehyde is as shown in the accompanying drawing. That is, it has been found that it is very effective to conduct separation by crystallization in obtaining substantially pure p-tolualdehyde from a mixture of tolualdehyde isomers.

The present invention provides a process for purifying p-tolualdehyde, which comprises cooling a solution of crude p-tolualdehyde containing o-tolualdehyde and m-tolualdehyde as impurities to a temperature of −6° to −60°C, thereby crystallizing p-tolualdehyde, and separating p-tolualdehyde crystals from mother liquor.

According to the present invention, a crude p-tolualdehyde solution having a mole fraction of at least 0.27, preferably at least 0.30 of p-tolualdehyde to the tolualdehyde isomers is applicable to obtain substantially pure p-tolualdehyde. The crude p-tolualdehyde solution having said mole fraction in the solution is cooled to the desired temperature, thereby crystallizing p-tolualdehyde as substantially pure crystals. The resulting p-tolualdehyde crystals are separated from o-tolualdehyde and m-tolualdehyde contained as impurities in the crude p-tolualdehyde solution, thereby obtaining p-tolualdehyde having a high purity.

Now, the present invention will be described by way of the accompanying drawing.

The single FIGURE is a solid-liquid equilibrium diagram of o-tolualdehyde and p-tolualdehyde.

In the FIGURE, curve 1 shows a relation between a mole fraction and freezing temperature of p-tolualdehyde, and curve 2 shows a relation between a mole fraction and freezing temperature of o-tolualdehyde. A shows a liquid phase, B a solid phase of p-tolualdehyde and C a solid phase of o-tolualdehyde.

As is apparent from FIGURE, a crystallization temperature, at which p-tolualdehyde is crystallized from a solution of tolualdehyde isomers according to the present invention, varies with a mole fraction of p-tolualdehyde in the solution, and is not definitely determined, but it is necessary to cool the solution to lower than the freezing point at the mole fraction of p-tolualdehyde in the solution. For example, when the mole fraction of p-tolualdehyde in the solution is 0.62, the solution must be cooled to lower than −30°C. The crystallization temperature must be made lower than the freezing point at the mole fraction of p-tolualdehyde in the solution, but generally the lower the temperature, the higher the crystallization yield of p-tolualdehyde. However, when the solution is cooled to lower than −60°C, o-tolualdehyde is crystallized as an eutectic crystal, and the purity of p-tolualdehyde is unpreferably lowered. In view of the foregoing facts, a crystallization temperature of −6° to −60°C is employed. That is, the crystallization temperature for crystallizing p-tolualdehyde crystals according to the present invention is determined from the solid-liquid equilibrium diagram as shown in FIGURE in a range of −6° to −60°C, in view of a composition of crude p- toluadehyde solution to be crystallized, and crystal yield (in other words final mother liquor composition).

According to the present invention, a mixture of tolualdehyde isomers is cooled to the desired temperature on the basis of a concentration (mole fraction) of p-tolualdehyde in the mixture, thereby crystallizing p-tolualdehyde, as described above, but the mixture is cooled to such a low temperature as lower than −30°C, depending upon the concentration (mole fraction) of p-tolualdehyde in the mixture. In that case, a viscosity of the solution is increased, and rapid formation of p-tolualdehyde crystals becomes rather difficult, and effective separation of the resulting p-tolualdehyde crystals from the mother liquor is not always easy to carry out. When the crystallization is carried out at such a low temperature, the increase in viscosity of the solution at the low temperature can be suppressed by using an appropriate solvent. The formation of p-tolualdehyde crystals and effective separation of p-tolualdehyde crystals from the mother liquor can be easily carried out thereby.

It is required for the appropriate solvent that the solvent is not so high in p-tolualdehyde solubility, readily separable from p-tolualdehyde, low in melting point, and low in viscosity even at a low temperature. The appropirate solent includes non-aromatic hydrocarbons having 1 to 9 carbon atoms, which are in a liquid state, that is, aliphatic hydrocarbons having 1 to 9 carbon atoms, preferably 2 to 8 carbon atoms or alicyclic hydrocarbons having 3 to 9 carbon atoms or preferably 5 to 8 carbon atoms, which are in a liquid state, more preferably, pentane, hexane and butane.

When such a solvent is used, it is usually necessary to lower the crystallization temperature rather than when the solvent is not used. The degree of the lowering the crystallization temperature depends upon crystallization conditions such as the kind of the solvent, a ratio of the solvent to the crude p-tolualdehyde, crystallization temperature, etc. For example, when 6 moles of hexane are used as a solvent per mole of the crude p-tolualdehyde, the temperature of initiating crystallization of p-tolualdehydde will be lower by 15°C than when the solvent is not used. An adequate ratio by mole of the solvent to the crude p-tolualdehyde is 0.5 to 30, preferably 1 to 10. Within said range, the crystallization temperature is lower by 5° to 40°C than when the solvent is not used, that is, −11°C to −100°C. In that case, the separation of p-tolualdehyde from the mother liquor can be readily carried out when the ratio of the solvent to the crude p-tolualdehyde is large, but when the ratio is too large, the crystallization temperature must be considerably lowered, and this is not commercially advantageous. Also, much more expense will be necessary for recovering the solvent, and the too large ratio is not preferable.

According to the present invention, p-tolualdehyde of a high purity can be obtained from the mixture of tolualdehyde isomers, but p-tolualdehyde of a much higher purity can be also obtained by washing the resulting p-tolualdehyde crystals with an appropriate washing agent. When the p-tolualdehyde crystals are washed, it is necessary to select such a washing temperature at which the p-tolualdehyde crystals will not be considerably melted, and o- and/or m-tolualdehyde adhering to the p-tolualdehyde crystals will not be crystallized. Such washing temperature must be lower by 5° to 70°C, preferably 5° to 30°C, than the crystallization temperature of pure p-tolualdehyde. The degree of lowering of the washing temperature is determined by crystallization conditions such as the use or nonuse of a solvent at the crystallization, kind of the solvent, crystallization temperature, etc., and separation conditions such as kind of the washing agent, ratio of the washing agent to the p-tolualdehyde crystals, contact time of the washing agent with the p-tolualdehyde crystals, etc.

It is required for the washing agent for washing the p-tolualdehyde crystals that a washing agent is not too high in p-tolualdehyde solubility, readily separable from p-tolualdehyde, low in melting point, and low in viscosity at a low temperature. The same material as mentioned above as the appropriate solvent can be used as the washing agent in the present invention.

When o- and/or m-tolualdehyde adhering to p-tolualdehyde crystals obtained by crystallization without using any solent according to the present invention is to be removed, the obtained p-tolualdehyde or raw p-tolualdehyde can be also used as the washing agent without using the so-called washing agent as described above.

Cooling of a mixture of tolualdehyde isomers to the desired temperature is carried out in the present invention by external cooling, that is, cooling of a crystallizer from its outside, inner cooling, that is, direct cooling of the solution, or simultaneous external and inner coolings. A cooling medium for the inner cooling includes, for example, solid or liquefied carbon dioxide, liquefied ethane, liquefied propane, liquefied ethylene, liquefied natural gas, etc. When a liquefied hydrocarbon such as liquefied ehtane, liquefied propane, etc. is used as a cooling medium, the cooling medium itself plays a role of said solvent, and advantageously lower the viscosity of solution and facilitate formation of p-tolualdehyde crystals.

p-Tolualdehyde, o-tolualdehyde and m-tolualdehyde handled in the present invention are liable to be oxidized with oxygen to form the corresponding toluic acids, and as a result the quality of p-tolualdehyde is lowered. Therefore, it is preferable in carrying out the present invention to flush a vessel with an inert gas such as nitrogen, etc., and use a gas-tight vessel, which is shielded from any contact with the atmosphere.

Now the present invention will be described in detail by way of examples.

EXAMPLE 1

25.9g (0.216 moles) of crude p-tolualdehyde (consisting of 97.75% of p-tolualdehyde and 2.25% of o-tolualdehyde) and 83.6g (1.16 moles) of pentane were placed in a 200-cc egg-plant type flask, and mixed. Then, the flask was dipped as such in a dry ice-methanol bath, and also dry ice was placed in the solution in the flask to conduct inner cooling. The flask was slowly cooled down to −47°C with cooling, and kept at that temperature for 30 minutes to crystallize p-tolualdehyde. The precipitated p-tolualdehyde crystals were filtered under a nitrogen atmosphere, while cooling a funnel with dry ice, and collected. The collected p-tolualdehyde crystals were melted, and then pentane adhering to the p-tolualdehyde crystals was distilled off in a rotary evaporator, whereby 24.6g of p-tolualdehyde product was obtained. The purity of the resulting p-tolualdehyde product was 99.7%.

EXAMPLE 2

23.5g (0.196 moles) of crude p-tolualdehyde (consisting of 97.75% of p-tolualdehyde and 2.25% of o- tolualdehyde) and 191.3g (2.66 moles) of pentane were placed in a 300-cc egg-plant type flask, and the flask was dipped in a dry ice-methanol bath, slowly cooled down to −37°C with good stirring in a nitrogen atmosphere, and kept at that temperature for 35 minutes to crystallize p-tolualdehyde. The precipitated p-tolualdehyde crystals were filtered under a nitrogen atmosphere, while cooling a funnel with dry ice, and collected. The collected p-tolualdehyde crystals were melted, and then pentane adhering to the p-tolualdehyde is distilled off in a rotary evaporator, whereby 21.4g of p-tolualdehyde product was obtained. The purity of the resulting p-tolualdehyde product was 99.9%.

EXAMPLE 3

25.9g (0.216 moles) of tolualdehyde consisting of 60.5% of p-tolualdehyde, 20.5% of o-tolualdehyde and 19% of m-tolualdehyde (p-tolualdehyde 15.7g, 0.131 mole; o-tolualdehyde 5.3g, 0.044 moles; m-tolualdehyde 4.9g, 0.041 mole) was placed in a test tube, and the test tube was dipped in a dry ice-methanol bath in a nitrogen atmosphere, and slowly cooled down to −52°C with good stirring and kept at that temperature for 1.5 hours to crystallize p-tolualdehyde. The precipitated p-tolualdehyde crystals were filtered while washing the crystals with 800g (9.30 mole) of hexane cooled to about −75°C in advance in a nitrogen atmosphere, and collected. The collected p-tolualdehyde crystals were melted, and then hexane adhering to the crystals was distilled off in a rotary evaporator, whereby 10.1g of p-tolualdehyde crystals were obtained. The purity of the resulting p-tolualdehyde product was 99.9%.

EXAMPLE 4

439g (3.66 moles) of crude p-tolualdehyde (consisting of 97.75% of p-tolualdehyde and 2.25% of o-tolualdehyde) and 877g (10.20 mole) of hexane were placed in a 2-l egg-plant type flask, and the flask was dipped in a dry ice-methanol bath as such, slowly cooled down to −25°C with good stirring in a nitrogen atmosphere, and kept at that temperature for 40 minutes to crystallize p-tolualdehyde. The precipitated p-tolualdehyde crystals were filtered, while washing the crystals with 700g (8.14 moles) of hexane cooled to about −30°C in advance in a nitrogen atmosphere, and collected. The collected p-tolualdehyde crystals were melted, and then hexane adhering to the crystals was distilled off in a rotary evaporator, whereby 214g of p-tolualdehyde product was obtained. The purity of the resulting p-tolualdehyde product was more than 99.9%.

EXAMPLE 5

32.1g. (0.268 moles) of tolualdehyde consisting of 73.2% of p-tolualdehyde and 26.8% of o-tolualdehyde (p-tolualdehyde 23.5g, 0.196 moles; o-tolualdehyde 8.6g, 0.072 moles) and 28.4g (0.283 moles) of n-heptane were placed in an egg-plant type flask, and the flask was dipped in a dry ice-methanol bath, slowly cooled down to −49°C with good stirring in a nitrogen atmosphere, and kept at that temperature for 50 minutes to crystallize p-tolualdehyde. The crystallized p-tolualdehyde crystals were filtered while washing the crystals with 660g (6.59 moles) of heptane cooled to about −75°C in advance in a nitrogen atmosphere, and collected. The collected p-tolualdehyde was melted, and then heptane adhering to the crystals was distilled off in a rotary evaporator, whereby 15.1g of p-tolualdehyde was obtained. The purity of the resulting p-tolualdehyde product was more than 99.9%.

EXAMPLE 6

38.7g of crude p-tolualdehyde (consisting of 97.75% of p-tolualdehyde and 2.25% of o-tolualdehyde) was placed in an egg-plant type flask, and the flask was dipped in a dry ice-methanol bath, cooled down to −33°C, while intermittently injecting liquefied propane into the flask to conduct inner cooling, and kept at that temperature for 30 minutes, while injecting liquefied propane into the flask. p-Tolualdehyde was crystallized thereby. A ratio of the liquefied propane to the crude p-tolualdehyde kept at −33°C was about 5:1 by mole, and about 1:1 by volume. The precipitated p-tolualdehyde crystals were filtered, while washing the crystals with about 500cc of liquefied propane, and collected. The collected p-tolualdehyde crystals amounted to 35.2g (0.293 moles) and p-tolualdehyde purity was 99.8%.

EXAMPLE 7

40.3g (0.336 moles) of tolualdehyde consisting of 82.0% of p-tolualdehyde and 18.0% of o-tolualdehyde (p-tolualdehyde 33.0g, 0.275 moles; o-tolualdehyde 7.3g, 0.061 moles) and 182g (2.11 mole) of m-hexane were placed in an egg-plant type flask, and the flask was dipped in a dry ice-methanol bath, slowly cooled down to −78°C with good stirring in a nitrogen atmosphere, and kept at that temperature for 1.5 hours to crystallize p-tolualdehyde. The precipitated p-tolualdehyde crystals were filtered in a nitrogen atmosphere while cooling a funnal with dry ice, and collected. The collected p-tolualdehyde was melted, and then n-hexane adhering to the crystals was distilled off in a rotary evaporator, whereby 29.6g of p-tolualdehyde was obtained. The purity of the resulting p-tolualdehyde was 99.5%.

EXAMPLE 8

32.0g (0.267 moles) of crude p-tolualdehyde (consisting of 87.0% of p-tolualdehyde) was placed in an egg-plant type flask, and the flask was dipped in a dry ice-methanol bath, slowly cooled down to −40°C with good stirring under a nitrogen atmosphere, and kept at that temperature for 30 minutes to crystallize p-tolualdehyde. The pricipitated p-tolualdehyde crystals were filtered while washing the crystals with 50g of 97.2% p-tolualdehyde under a nitrogen atmosphere, and collected, whereby 24.4g of p-tolualdehyde crystals were obtained. The purity of the resulting p-tolualdehyde product was 99.6%.

EXAMPLE 9

93.0g (0.775 moles) of crude p-tolualdehyde (consisting of 87.0% of p-tolualdehyde) was placed in an egg-plant type flask, and the flask was dipped in a dry ice-methanol bath, slowly cooled down to −43°C with stirring under a nitrogen atmosphere, and kept at that temperature for 30 minutes to crystallize p-tolualdehyde. The precipitated p-tolualdehyde crystals were filtered under a nitrogen atmosphere and removed sufficiently of mother liquor from the crystal surface and collected, whereby 64.0g of p-tolualdehyde crystals was obtained.

The purity of the resulting p-tolualdehyde product was 99.3%.

What is claimed is:

1. A process for purifying p-tolualdehyde, which comprises cooling a mixture of tolualdehyde isomers consisting essentially of p-tolualdehyde, o-tolualdehyde and m-tolualdehyde and having a mole fraction of at lest 0.27 of p-tolualdehyde on the basis of the total isomers to a crystallization temperature of −6° to −60°C, thereby crystallizing p-tolualdehyde, and separating the resulting p-tolualdehyde crystals from mother liquor.

2. A process according to claim 1, where the mole fraction of p-tolualdehyde is at least 0.30.

3. A process according to claim 1, wherein the resulting p-tolualdehyde crystals are further washed with a washing agent.

4. A process according to claim 3, wherein the washing temperature is lower by 5° to 70°C than the crystallization temperature of pure p-tolualdehyde.

5. A process according to claim 3, wherein the washing agent is an aliphatic hydrocarbon having 1 to 9 carbon atoms or an alicyclic hydrocarbon having 3 to 9 carbon atoms.

6. A process according to claim 5, wherein the washing agent is pentane, hexane or butane.

7. A process according to claim 3, wherein the resulting p-tolualdehyde crystals are melted and the remaining washing agent is removed by distillation.

8. A process for purifying p-tolualdehyde, which comprises adding an aliphatic or alicyclic hydrocarbon as a solvent to a mixture of tolualdehyde isomers consisting essentially of p-tolualdehyde, o-tolualdehyde and m-tolualdehyde and having a mole fraction of at least 0.27 of p-tolualdehyde on the basos of the total isomers, cooling the mixture to a crystallization temperature of −11°C to −100°C, thereby crystallizing p-tolualdehyde, and separating the resulting p-tolualdehyde crystals from mother liquor.

9. A process according to claim 8, wherein 0.5 to 30 moles of the solvent are added per one mole of the mixture of tolualdehyde isomers.

10. A process according to claim 9, wherein 1 to 10 moles of the solvent are added per one mole of the mixture of tolualdehyde isomers.

11. A process according to claim 8, wherein the solvent is an aliphatic hydrocarbon having 1 to 9 carbon atoms or an alicyclic hydrocarbon having 3 to 9 carbon atoms.

12. A process according to claim 11, wherein the solvent is butane, hexane or heptane.

13. A process according to claim 8, wherein the mole fraction of p-tolualdehyde is at least 0.30.

14. A process according to claim 8, wherein the resulting p-tolualdehyde is further washed with a washing agent.

15. A process according to claim 14, wherein the washing temperature is lower by 5° to 70°C than the crystallization temperature of pure p-tolualdehyde.

16. A process according to claim 14, wherein the washing agent is an aliphatic hydrocarbon having 1 to 9 carbon atoms or an alicyclic hydrocarbon having 3 to 9 carbon atoms.

17. A process according to claim 16, wherein the washing agent is pentane, hexane or butane.

18. A process according to claim 8, wherein the resulting p-tolualdehyde crystals are melted and the remaining solvent is removed by distillation.

* * * * *